United States Patent
Kim et al.

(10) Patent No.: US 12,296,288 B2
(45) Date of Patent: May 13, 2025

(54) MULTI-COMPONENT MIXTURE SEPARATION SYSTEM

(71) Applicant: LG CHEM, LTD., Seoul (KR)

(72) Inventors: Sung Kyun Kim, Daejeon (KR); Sung Kyu Lee, Daejeon (KR); Tae Woo Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 18/020,873

(22) PCT Filed: Jun. 16, 2022

(86) PCT No.: PCT/KR2022/008577
§ 371 (c)(1),
(2) Date: Feb. 10, 2023

(87) PCT Pub. No.: WO2023/043003
PCT Pub. Date: Mar. 23, 2023

(65) Prior Publication Data
US 2024/0299859 A1    Sep. 12, 2024

(30) Foreign Application Priority Data
Sep. 14, 2021   (KR) .................... 10-2021-0122586

(51) Int. Cl.
*B01D 3/14*   (2006.01)
*B01D 3/00*   (2006.01)
*B01D 3/32*   (2006.01)
*B01D 5/00*   (2006.01)
*B01D 17/02*  (2006.01)

(52) U.S. Cl.
CPC ............. *B01D 3/141* (2013.01); *B01D 3/008* (2013.01); *B01D 3/143* (2013.01); *B01D 3/32* (2013.01); *B01D 5/0063* (2013.01); *B01D 17/02* (2013.01)

(58) Field of Classification Search
CPC ..................................... B01D 3/141
See application file for complete search history.

(56) References Cited

U.S. PATENT DOCUMENTS 5,709,780 A   1/1998   Ognisty et al.
5,755,933 A   5/1998   Ognisty et al.
(Continued)

FOREIGN PATENT DOCUMENTS

CN   103328464 A   3/2015
CN   105142747 A   1/2018
(Continued)

*Primary Examiner* — Jonathan Luke Pilcher
(74) *Attorney, Agent, or Firm* — Bryan Cave Leighton Paisner LLP

(57) ABSTRACT

The present disclosure provides a multi-component mixture separation system including a distillation column including a first section and a second section separated by a partition wall, and a phase separator receiving a lower discharge stream of the second section and separating the stream into an aqueous phase and an oil phase, and refluxing a portion of the separated aqueous phase or oil phase to the first section, in which the first section includes a chimney tray provided on an upper portion, and the first section is fed with a feed stream containing three or more components to separate high-boiling point component to a lower portion, and a gaseous component moves to the second section.

11 Claims, 4 Drawing Sheets

(56) References Cited

U.S. PATENT DOCUMENTS

| | | | |
|---|---|---|---|
| 6,930,206 B1* | 8/2005 | Groten | C07C 41/06 203/28 |
| 7,014,833 B2* | 3/2006 | Groten | C07C 5/2506 203/28 |
| 7,026,517 B2* | 4/2006 | Groten | C07C 5/27 568/697 |
| 7,030,277 B2* | 4/2006 | Groten | B01D 3/009 203/28 |
| 7,358,388 B2* | 4/2008 | Woelfert | C07C 263/20 560/352 |
| 7,410,555 B2* | 8/2008 | Groten | C07C 2/06 203/29 |
| 8,088,944 B2* | 1/2012 | Woelfert | C07C 263/10 560/352 |
| 10,377,690 B1* | 8/2019 | Owens | C07C 45/74 |
| 10,399,004 B2* | 9/2019 | Hoyme | B01D 3/36 |
| 10,486,080 B2 | 11/2019 | Choo et al. | |
| 10,526,545 B2* | 1/2020 | Eizenga | B01D 3/38 |
| 10,792,583 B2* | 10/2020 | Schulz | B01D 3/4233 |
| 10,835,837 B2* | 11/2020 | Hoyme | C07C 45/80 |
| 11,261,150 B2* | 3/2022 | Rolez | C07C 213/10 |
| 2004/0204614 A1* | 10/2004 | Groten | B01D 3/141 568/38 |
| 2004/0210090 A1* | 10/2004 | Groten | C07C 5/2506 568/38 |
| 2004/0210091 A1* | 10/2004 | Groten | C07C 319/18 568/38 |
| 2004/0210092 A1* | 10/2004 | Groten | C07C 5/27 568/38 |
| 2004/0210093 A1* | 10/2004 | Groten | C07C 5/27 203/29 |
| 2006/0135810 A1* | 6/2006 | Wolfert | B01D 3/141 560/352 |
| 2007/0015934 A1* | 1/2007 | Wolfert | B01D 3/141 560/352 |
| 2018/0065061 A1* | 3/2018 | Hoyme | C07C 7/06 |
| 2018/0119023 A1* | 5/2018 | Eizenga | B01D 3/141 |
| 2019/0247766 A1* | 8/2019 | Hoyme | B01D 3/143 |
| 2019/0299116 A1* | 10/2019 | Schulz | C07C 37/74 |
| 2021/0300857 A1* | 9/2021 | Rolez | C07C 213/06 |

FOREIGN PATENT DOCUMENTS

| | | |
|---|---|---|
| CN | 111298471 A | 6/2020 |
| JP | 9-136855 A | 5/1997 |
| JP | H09-124536 A | 5/1997 |
| JP | 10-57703 A | 3/1998 |
| JP | 2000-239228 A | 9/2000 |
| KR | 10-0231644 B1 | 11/1999 |
| KR | 10-1092199 B1 | 12/2011 |
| KR | 10-1325821 B1 | 11/2013 |
| KR | 10-1530102 B1 | 6/2015 |
| KR | 10-2015-0120500 A | 10/2015 |
| KR | 10-2017-0029311 A | 3/2017 |
| KR | 10-1784456 B1 | 10/2017 |
| KR | 10-1805324 B1 | 12/2017 |
| KR | 10-2019-0056738 A | 5/2019 |
| KR | 10-2020-0133789 A | 11/2020 |
| KR | 10-2021-0029251 A | 3/2021 |
| RU | 2717093 C1 | 3/2020 |

* cited by examiner

【FIG. 1】
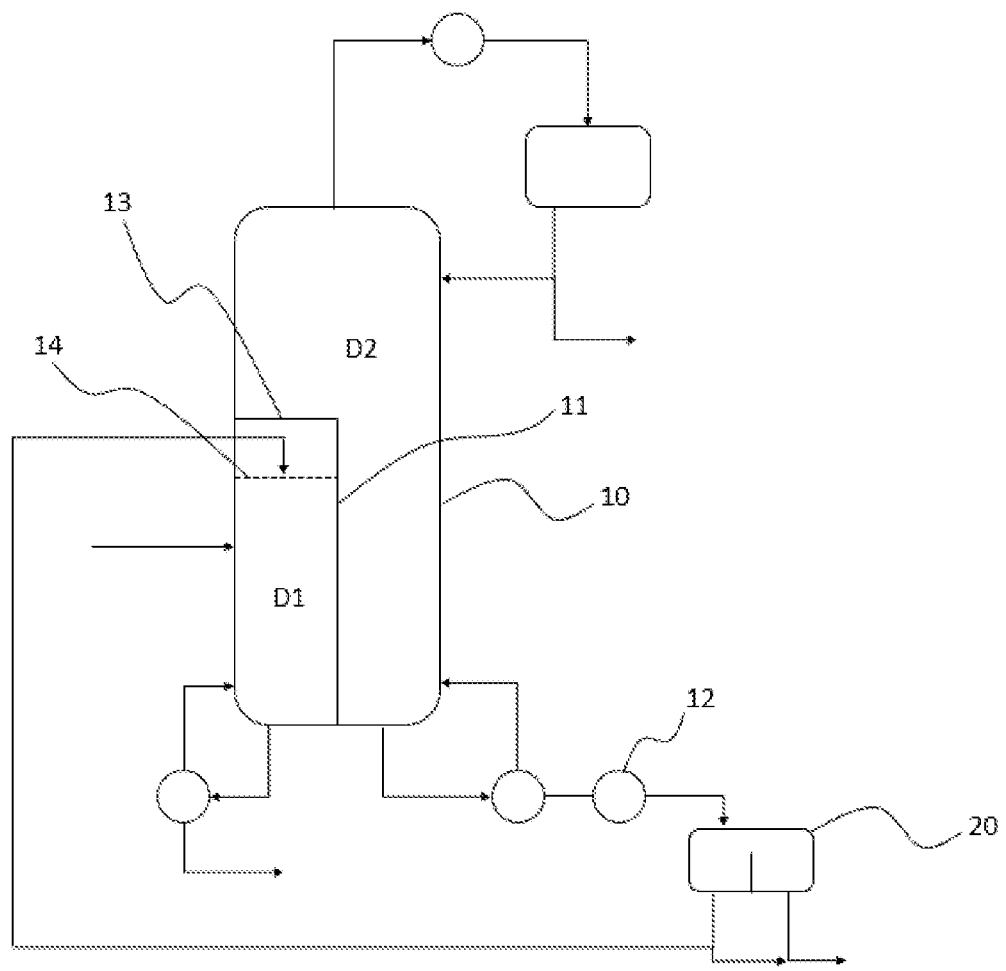

[FIG. 2]
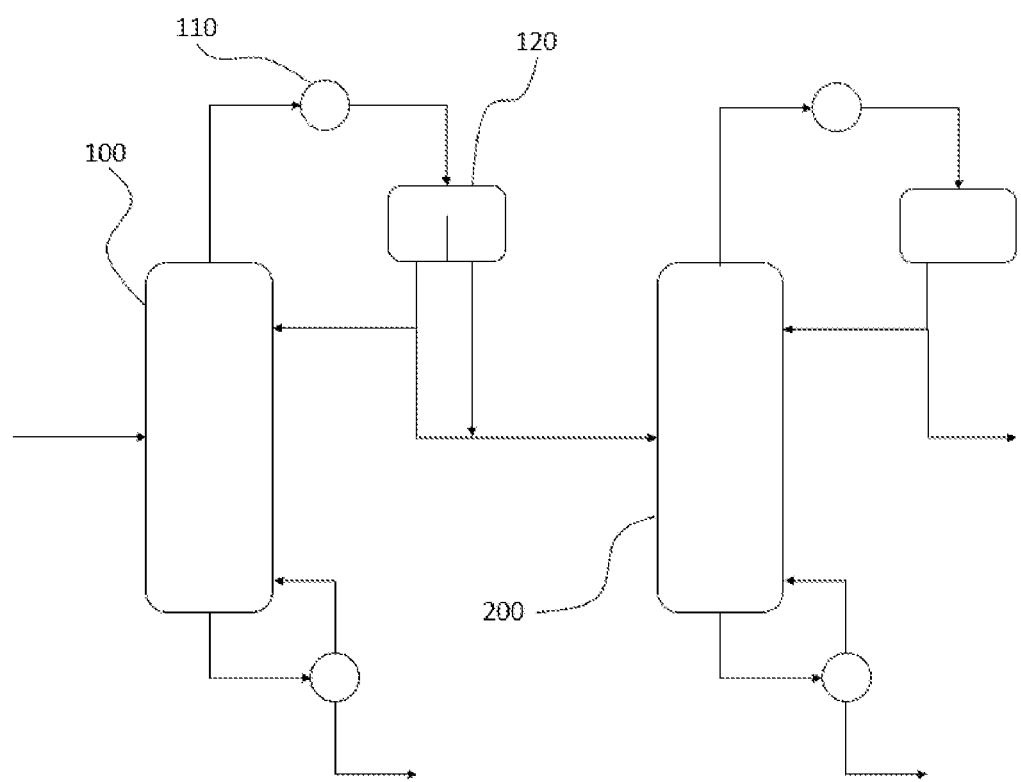

[FIG. 3]
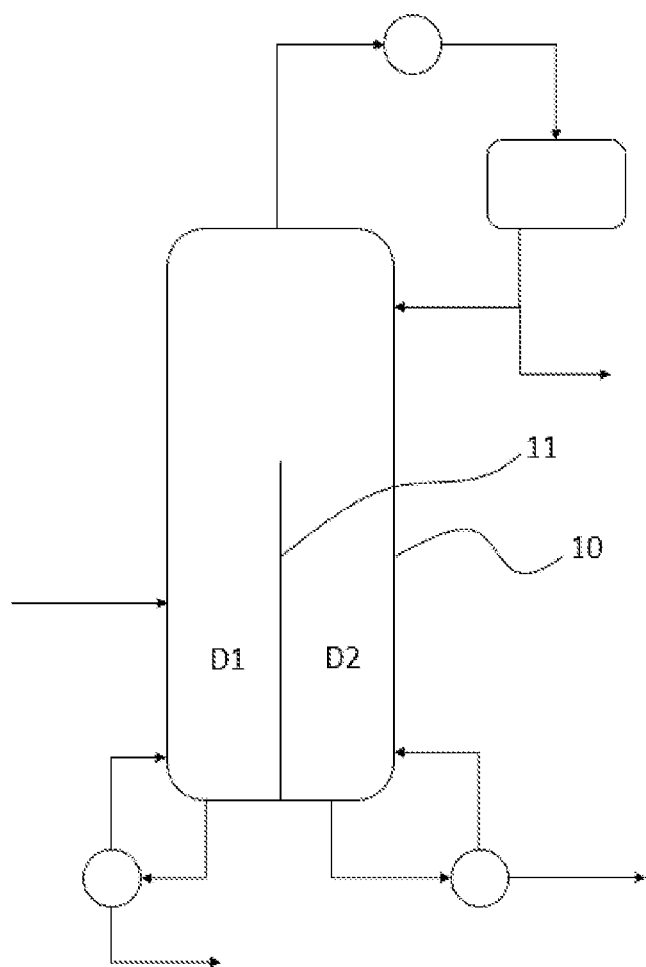

【FIG. 4】
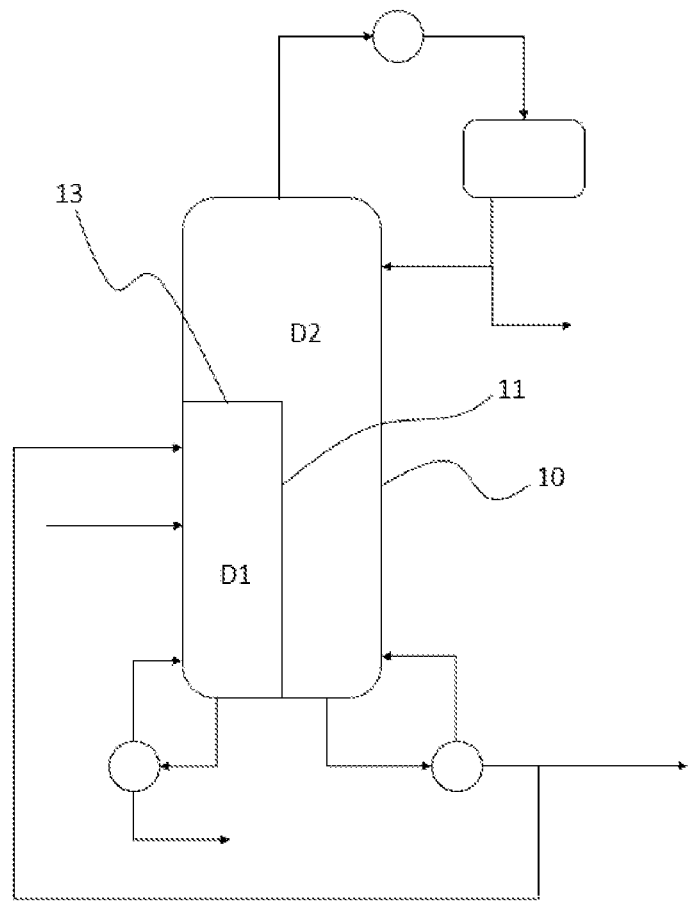

MULTI-COMPONENT MIXTURE SEPARATION SYSTEM

CROSS REFERENCE TO PRIOR APPLICATIONS

This application is a National Phase entry pursuant to 35 U.S.C. § 371 of International Application No. PCT/KR2022/008577, filed on Jun. 16, 2022, and claims the benefit of and priority to Korean Patent Application No. 10-2021-0122586, filed on Sep. 14, 2021, the entire contents of which are incorporated by reference in their entirety for all purposes as if fully set forth herein.

TECHNICAL FIELD

The present disclosure relates to a multi-component mixture separation system, and more particularly, to a multi-component mixture separation system capable of simplifying a process and saving energy in separating a multi-component mixture containing three or more components.

BACKGROUND

A process of separating a desired component from other components in a mixture containing three or more components generated through a reaction and recovering unreacted substances may be achieved by a distillation operation sequence. This sequence may include a distillation column for separating all of low-boiling point components, medium-boiling point components, and high-boiling point components from the desired mixture. In order to separate the desired component from the mixture containing three or more components, two or more distillation columns are required.

For example, the mixture containing three or more components may be fed to a distillation column of a front stage, the high-boiling point components may be separated into a lower portion in the distillation column of the front stage, the low-boiling point components and the medium-boiling point components may be fed to a distillation column of a rear stage, the low-boiling point components may be separated into an upper portion in the distillation column of the rear stage, and the medium-boiling point components may be separated to a lower portion, respectively. In addition, the mixture containing three or more components may be fed to the distillation column of the front stage, the low-boiling point components may be separated into an upper portion in the distillation column of the front stage, the medium-boiling point components and the high-boiling point components may be separated to a lower portion, the medium-boiling point and the high-boiling point components may be fed to the distillation column of the rear stage, the medium-boiling point components may be separated into an upper portion in the distillation column of the rear stage, and the high-boiling point components may be separated to a lower portion, respectively.

As such, in order to separate the mixture containing three or more components, two or more distillation columns may be required, and two or more additional devices may also be required, which causes a problem in that the process becomes complicated, and when a stream moves between the two or more distillation columns, unnecessary cooling and heating may be required, which causes a problem in that the number of devices and energy consumption increase.

The background description provided herein is for the purpose of generally presenting context of the disclosure. Unless otherwise indicated herein, the materials described in this section are not prior art to the claims in this application and are not admitted to be prior art, or suggestions of the prior art, by inclusion in this section.

DISCLOSURE

Technical Problem

In order to solve the problems mentioned in the technology that is the background of the invention, the present disclosure provides a multi-component mixture separation system that uses a distillation column equipped with a partition wall to separate a mixture containing three or more components and control a feed end of a stream refluxed to a mixture containing three or more components to separate the mixture, thereby preventing unnecessary cooling and heating to simplify a process and save energy.

Technical Solution

In one general aspect, a multi-component mixture separation system includes a distillation column including a first section and a second section separated by a partition wall, and a phase separator receiving a lower discharge stream of the second section and separating the lower discharge stream into an aqueous phase and an oil phase, and refluxing a portion of the separated aqueous phase or oil phase to the first section, in which the first section includes a chimney tray provided on an upper portion of the first section, and the first section is fed with a feed stream containing three or more components to separate high-boiling point component to a lower portion, and a gaseous component moves to the second section.

Advantageous Effects

According to the present disclosure, a multi-component mixture separation system uses one distillation column equipped with a partition wall, moves gaseous components from a first section to a second section of the distillation column but prevents liquefied components from moving from the second section to the first section, and controls a feed end of a stream refluxed from a phase separator to the distillation column to separate a mixture, thereby simplifying a process to reduce the number of devices and preventing unnecessary cooling and heating to save energy.

BRIEF DESCRIPTION OF THE DRAWINGS

FIG. 1 is a process flow diagram of a multi-component mixture separation system according to an embodiment of the present disclosure.

FIGS. 2 to 4 are process flow diagrams of a multi-component mixture separation system according to Comparative Examples, respectively.

DETAILED DESCRIPTION

Terms and words used in the present specification and claims are not to be construed as a general or dictionary meaning but are to be construed as meaning and concepts meeting the technical ideas of the present disclosure based on a principle that the inventors can appropriately define the concepts of terms in order to describe their own inventions in best mode.

In the present disclosure, the term 'stream' may mean a flow of a fluid in a process, and may also mean a fluid itself flowing in a pipe. Specifically, the stream may mean both the fluid itself and the flow of the fluid flowing within the pipe connecting each device. In addition, the fluid may contain any one or more components of a gas, a liquid, and a solid.

Hereinafter, the present disclosure will be described in more detail with reference to FIG. 1 to help the understanding of the present disclosure.

According to the present disclosure, a multi-component mixture separation system is provided. The multi-component mixture separation system includes a distillation column 10 including a first section D1 and a second section D2 separated by a partition wall 11, and a phase separator 20 receiving a lower discharge stream of the second section D2 and separating the stream into an aqueous phase and an oil phase, and refluxing a portion of the separated aqueous phase or oil phase to the first section D1, in which the first section D1 includes a chimney tray 13 provided on an upper portion, and the first section D1 is fed with a feed stream containing three or more components to separate high-boiling point component to a lower portion, and a gaseous component moves to the second section D2.

A process of separating a desired component from other components in a mixture containing three or more components generated through the existing polymerization reaction and recovering unreacted substances may be achieved by a distillation operation sequence. This sequence may include a distillation column for separating all of low-boiling point components, medium-boiling point components, and high-boiling point components from the desired mixture. In order to separate the desired component from the mixture containing three or more components, two or more distillation columns are required.

For example, a mixture containing three or more components may be fed to a distillation column of a front stage, the high-boiling point component may be separated into the lower portion in the distillation column of the front stage, the low-boiling point component and the medium-boiling point component may be fed to a distillation column of a rear stage, the low-boiling point component may be separated into an upper portion in the distillation column of the rear stage, and the medium-boiling point component may be separated to the lower portion, respectively. In addition, the mixture containing three or more components may be fed to the distillation column of the front stage, the low-boiling point component may be separated into an upper portion in the distillation column of the front stage, the medium-boiling point component and the high-boiling point component may be separated to the lower portion, the medium-boiling point component and the high-boiling point component may be fed to the distillation column rear stage, the medium-boiling point component may be separated into an upper portion in the distillation column of the rear stage, and the high-boiling point component may be separated to the lower portion, respectively.

As such, in order to separate the mixture containing three or more components, two or more distillation columns may be required, and two or more additional devices may also be required, which causes a problem in that the process becomes complicated, and when a stream moves between the two or more distillation columns, unnecessary cooling and heating may be required, which causes a problem in that the number of devices and energy consumption increase.

On the other hand, in the present disclosure, one distillation column 10 provided with a partition wall 11 is used, and gaseous components move from the first section D1 to the second section D2 of the distillation column 10. However, the present disclosure provides a multi-component mixture separation system that prevents the liquefied component from moving from the second section D2 to the first section D1 and controls the feed end of the stream refluxed from the phase separator 20 to the distillation column 10 to separate the mixture, thereby reducing the number of devices by simplifying the process and preventing unnecessary cooling and heating to save energy.

According to an embodiment of the present disclosure, the distillation column 10 may be fed with a feed stream containing components to separate each component. For example, the feed stream may contain 3 to 5 components, 3 to 4 components, or 3 components, and as a specific example, the feed stream may contain 3 components.

The inside of the distillation column 10 may be separated into two sections due to the partition wall 11. Specifically, the distillation column 10 may be partitioned into the first section D1 and the second section D2 through a partition wall 11, and the distillation in the first section D1 and the second section D2 may be performed independently.

The partition wall 11 may be formed to extend upwardly from a lower end of the distillation column 10, for example, and an upper region of the partition wall 11 may communicate.

The partition wall 11 may extend vertically from the lower end of the distillation column 10 to a height spaced apart from an upper end of the distillation column 10 without reaching the upper end of the distillation column 10, for example. Specifically, the partition wall 11 extends from the lower end of the distillation column 10 to a certain height in an upper direction, that is, in a longitudinal direction of the distillation column 10, and the communication between the first section D1 and the second section D2 in the lower region of the distillation column 10 may be blocked through the partition wall 11. In this case, the height of the partition wall 11 may be, for example, 30% or more, 40% or more, 50% or more and 60% or less, 70% or less, or 80% or less of the height of the distillation column 10. By designing the height of the partition wall 11 within the above range, it is possible to separate the low-boiling point component, the medium-boiling point component, and the high-boiling point component for each boiling point in one column. According to an embodiment of the present disclosure, the distillation column 10 is partitioned through the partition wall 11, and the first section D1 partitioned through the partition wall 11 may further include a chimney tray 13 provided on the upper portion. The chimney tray 13 may be formed to correspond to an upper area of the first section D1 partitioned by the partition wall 11.

The chimney tray 13 may include a plurality of chimneys communicating the gaseous component rising from the lower region of the chimney tray 13 to the upper region, and prevent the liquefied component that may be accumulated in the chimney tray 13 from penetrating into the lower region of the chimney tray 13. Through this, the chimney tray 13 may move the gaseous component from the first section D1 to the second section D2 of the distillation column 10, but prevent the liquefied component from moving from the second section D2 to the first section D1. Specifically, the communication of the liquefied component may be blocked between the first section D1 and the second section D2 of the distillation column 10 through the chimney tray 13, and the gaseous component may be made to communicate only from the first section D1 to the second section D2 of the distillation column 10. In this way, the gaseous component of the first section D1 of the distillation column 10 moves directly to the second section D2 without a separate condensation and heating step, thereby preventing the use of unnecessary energy to save energy used in the process.

When the distillation column 10 is partitioned into the first section D1 and the second section D2 through the partition wall 11, the partition wall 11 and the chimney tray 13 may be described mainly. For example, the first section D1 of the distillation column 10 may mean a section positioned in the lower portion with respect to the chimney tray 13, and as a more specific example, may mean a section partitioned through the partition wall 11 on the side while positioned in the lower portion with respect to the chimney tray 13. In addition, the second section D2 of the distillation column 10 may mean a section positioned in the upper portion with respect to the chimney tray 13, and as a more specific example, may mean a section partitioned through the partition wall 11 while positioned in the upper portion with respect to the chimney tray 13.

According to an embodiment of the present disclosure, the first section D1 may further include a liquid distribution device 14 provided under the chimney tray 13. The liquid distribution device 14 may serve to evenly spread the liquid material of the upper portion to the lower portion, and may communicate the gaseous component of the lower portion to the upper portion. Specifically, the chimney tray 13 is provided above the first section D1, so that the liquefied component falling from the upper portion to the lower portion of the first section D1 does not exist. Therefore, for the separation of the feed stream in the first section D1, the liquid distribution device 14 is disposed, and the refluxed stream from the phase separator 20 is fed to a position between the chimney tray 13 and the liquid distribution device 14, and thus, liquefied components may be distributed and sprayed to the lower portion of the liquid distribution device 14. In this case, the substance is transferred by bringing the gaseous component boiled in the lower portion of the liquid distribution device 14 into contact with the liquid component sprayed to the lower portion through the liquid distribution device 14, so the separation may effectively occur.

According to an embodiment of the present disclosure, the feed stream containing three or more components fed to the distillation column 10 may be fed to a position lower than the liquid distribution device 14 provided in the first section D1 of the distillation column 10. In this case, the feed stream may contain the low-boiling point component, the medium-boiling point component, and the high-boiling point component for each boiling point.

The feed stream fed to the distillation column 10 is distilled in the first section D1, and the vaporized gaseous component rising through the distillation may pass through the chimney tray 13 to move to the second section D2. In addition, the liquefied component in the first section D1 of the distillation column 10 may be separated into the lower portion of the distillation column 10, and the lower discharge stream separated into the lower portion in the first section D1 of the distillation column 10 may contain the high-boiling point component of the feed stream. In this case, the operating condition of the first section D1 is that the high-boiling point component in the feed stream may be separated into the lower portion, and the medium-boiling point component and the low-boiling point component may be vaporized and raised to the upper portion of the first section D1 and may be appropriately adjusted to move to the second section D2.

The lower discharge stream of the first section D1 is partially refluxed through the conventional reboiler, and the remaining components may be recovered.

The gaseous component moving to the upper portion of the first section D1 of the distillation column 10 may move to the second section D2 and subjected to additional distillation. In this case, the gaseous component moving to the second section D2 may contain the medium-boiling point component and the low-boiling point component of the feed stream. The medium-boiling point component and the low-boiling point component may be separated through the distillation in the second section D2, and specifically, the low-boiling point component may be separated into the upper portion of the second section D2, and the medium-boiling point component may be separated into the lower portion.

The upper discharge stream discharged to the upper portion of the second section D2 may contain the low-boiling point component of the feed stream. In this case, after the upper discharge stream of the second section D2 may be condensed in the conventional manner, some of the stream may be refluxed and the remaining stream may be recovered.

The lower discharge stream separated into the lower portion of the second section D2 of the distillation column 10 is fed to the phase separator 20, and then, the medium-boiling point component may be separated from any one or more of the aqueous phase and the oil phase separated in the phase separator 20. For example, some of the lower discharge stream of the second section D2 of the distillation column 10 may be refluxed through the conventional reboiler, and the remaining stream may be fed to the phase separator 20. In this case, the remaining stream other than the stream refluxed through the reboiler may pass through, for example, a cooler 12, and then, may be fed to the phase separator 20. The cooler 12 may cool the stream fed to the phase separator 20.

The phase separator 20 may be a device for separating an aqueous phase and an oil phase. For example, it is possible to separate the aqueous phase and the oil phase of the lower discharge stream of the second section D2 of the distillation column 10, and reflux some of the separated aqueous phase or oil phase to the first section D1 of the distillation column 10. In this case, some streams of the separated aqueous phase and oil phase may be refluxed to the first section D1 of the distillation column 10, and the medium-boiling point component may be separated from and recovered to streams other than the stream refluxed to the first section D1. As a specific example, some of the aqueous phase may be refluxed to the first section D1, and the medium-boiling point component may be separated from the remaining aqueous phase and oil phase not refluxed to the first section D1 of the aqueous phase.

The stream refluxed from the phase separator 20 to the first section D1 of the distillation column 10 may be fed to a position higher than a height at which the feed stream is fed in the first section D1. In this case, it is possible to effectively separate by maximizing the substance transfer effect in the first section D1.

The stream refluxed from the phase separator 20 to the first section D1 of the distillation column 10 may be refluxed to a position between the chimney tray 13 and the liquid distribution device 14 provided above the first section D1. Specifically, the stream refluxed from the phase separator 20 to the first section D1 of the distillation column 10 may be refluxed to a position lower than the chimney tray 13 provided above the first section D1 and higher than the liquid distribution device 14. In this case, the liquefied stream refluxed from the phase separator 20 may be prevented from flowing out to the second section D2, and the liquefied stream refluxed from the phase separator 20 may be evenly sprayed to the lower portion using the liquid distribution device 14, thereby further increasing the separation effect through the substance transfer.

According to an embodiment of the present disclosure, the multi-component mixture separation system can be used to separate each desired component from crude hydroxypivaldehyde, crude phenol, crude isopropyl alcohol, crude acrylic acid, and the like. As a specific example, the multi-component mixture separation system may be used to separate each component from crude hydroxypivaldehyde containing hydroxypivaldehyde and iso-butylaldehyde.

Specifically, the hydroxypivaldehyde (HPA) is prepared by an aldol condensation reaction between iso-butylaldehyde (i-BAL) and an aqueous formaldehyde solution, and the crude hydroxypivaldehyde produced through the aldol condensation reaction may contain hydroxypivaldehyde, unreacted iso-butylaldehyde, and by-products as the desired products. In this case, the aldol condensation reaction may be performed under the conventional hydroxypivaldehyde production conditions, may be performed in the presence of a catalyst, and if necessary, an additive may be used.

The crude hydroxypivaldehyde may be fed to the first section D1 of the distillation column 10 as a feed stream, the hydroxypivaldehyde may be separated into the lower portion of the first section D1 through the distillation in the first section D1, and the unreacted iso-butylaldehyde and by-products pass through the chimney tray 13 as gaseous components and move directly to the second section D2 to save the energy required for the unnecessary cooling and heating.

In the second section D2 of the distillation column 10, the unreacted iso-butylaldehyde may be separated into the upper portion, and the lower discharge stream may be fed to the phase separator 20 through the reboiler and the cooler 12.

The height of the partition wall 11 provided in the distillation column 10 may be appropriately adjusted according to the components of the feed stream.

The aqueous phase and the oil phase are separated in the phase separator 20, and some of the separated aqueous phase may be refluxed to the first section D1 of the distillation column 10, more specifically, a height positioned between the chimney tray 13 of the first section D1 and the liquid distribution devices 14. In addition, the by-products may be separated from the aqueous phase and the oil phase that are not refluxed to the first section D1 in the phase separator 20.

The stream fed to the phase separator 20 contains the by-products, and a small amount of hydroxypivaldehyde may be contained in the aqueous phase component of the by-product. The oil phase and the aqueous phase may be separated by the phase separator 20, and some of the aqueous phase may be recovered and refluxed to the first section D1 of the distillation column 10, and may be further subjected to the distillation process to be recovered to the lower portion of the first section D1. As a result, it is possible to increase the production of the hydroxypivaldehyde, and prevent the by-products produced by the aldol condensation reaction from increasing.

Hereinabove, the multi-component mixture separation system according to the present disclosure has been shown in the description and drawings, but the above drawings and the description describe and illustrate only the essential components for understanding the present disclosure. In addition to the processes and apparatus illustrated in the above description and drawings, processes and apparatus not separately described and shown may be appropriately applied and used to implement the multi-component mixture separation system according to the present disclosure.

Hereinafter, the present disclosure will be described in more detail with through Examples. However, the following examples are for illustrating the present disclosure, and it is clear to those skilled in the art that various changes and modifications are possible within the scope and spirit of the present disclosure, and the scope of the present disclosure is not limited only thereto.

EXAMPLES

Example 1

As in the process flow diagram illustrated in FIG. 1, a multi-component mixture separation system was simulated using Aspen Plus of Aspen Company.

Specifically, crude hydroxypivaldehyde was fed as a feed stream to a first section D1 of a distillation column 10. In this case, the feed stream contains hydroxypivaldehyde, unreacted iso-butylaldehyde and by-products. In addition, distillation column 10 was partitioned into a first section D1 and a second section D2 through a partition wall 11, a chimney tray 13 was provided above the first section D1, a liquid distribution device 14 was provided under the chimney tray 13, and the feed stream was fed to a lower position than the liquid distribution device 14.

Some of the lower discharge stream from the first section D1 of the distillation column 10 was refluxed by using a reboiler, hydroxypivaldehyde was separated into the remaining stream, and the gaseous component moved directly to the second section D2.

In the second section D2, some of the upper discharge stream was refluxed by using a condenser, unreacted iso-butylaldehyde was separated into the remaining stream, and by-products were separated into a lower portion.

Some of the lower discharge stream of the second section D2 containing the by-products was refluxed by using the reboiler and the remaining stream was fed to the phase separator 20 through the cooler 12.

An oil phase and an aqueous phase were separated by the phase separator 20, some of the aqueous phase was fed to a position between the chimney tray 13 and the liquid distribution device 14 of the first section D1 of the distillation column 10, and the by-products were separated into the remaining aqueous and oil phases.

Results of measuring a recovery rate of hydroxypivaldehyde (HPA) recovered from the lower portion of the first section D1 of the distillation column 10, a recovery rate of iso-butylaldehyde (i-BAL) recovered from the upper portion of the second section D2, energy consumption used in the distillation column 10, and content of 2,2,4-trimethyl-1,3-pentanediol (TMPD) in the lower discharge stream of the first section D1 separating hydroxypivaldehyde were shown in the following Table 1.

COMPARATIVE EXAMPLES

Comparative Example 1

As in the process flow diagram illustrated in FIG. 2, simulations were performed using Aspen Plus manufactured by Aspen Corporation.

Specifically, crude hydroxypivaldehyde was fed as a feed stream to the first distillation column 100. At this time, the components of the feed stream are the same as in Example 1.

Some of a lower discharge stream of the first distillation column 100 was refluxed by using a reboiler, and hydroxypivaldehyde was recovered to the remaining steam, an upper discharge stream was fed to the condenser 110 for condensing and then fed to a phase separator 120, some of an aqueous phase in the phase separator 120 was refluxed to a first distillation column 100, and the aqueous phase and oil phase not refluxed to the first distillation column 100 were fed to a second distillation column 200.

In the second distillation column 200, some of the upper discharge stream was refluxed by using the reboiler, iso-butylaldehyde was recovered to the remaining stream, some of the lower discharge stream was refluxed by using the reboiler, and the by-products were separated into the remaining stream.

Results of measuring a recovery rate of hydroxypivaldehyde recovered from a lower portion of the first distillation column 100, a recovery rate of iso-butylaldehyde recovered from an upper portion of the second distillation column 200, energy consumption used in the first distillation column 100 and the second distillation column 200, and content of 2,2,4-trimethyl-1,3-pentanediol (TMPD) in the lower discharge stream of the first distillation column 100 separating the hydroxypivaldehyde were shown in the following Table 1.

Comparative Example 2

As in the process flow diagram illustrated in FIG. 3, simulations were performed using Aspen Plus manufactured by Aspen Corporation.

Specifically, crude hydroxypivaldehyde was fed as a feed stream to a first section D1 of a distillation column 10. At this time, the components of the feed stream are the same as in Example 1. In addition, the distillation column 10 was partitioned into a first section D1 and a second section D2 through a partition wall 11.

Some of the lower discharge stream of the first section D1 was refluxed by using a reboiler, and hydroxypivaldehyde was separated into the remaining stream.

Some of the upper discharge stream of the distillation column 10 was refluxed by using a condenser, and unreacted iso-butylaldehyde was separated into the remaining stream.

Some of the lower discharge stream of the second section D2 was refluxed by using a reboiler, and by-products were separated into the remaining stream.

Results of measuring a recovery rate of hydroxypivaldehyde (HPA) recovered from the lower portion of the first section D1 of the distillation column 10, a recovery rate of iso-butylaldehyde (i-BAL) recovered to the upper portion of the distillation 10, energy consumption used in the distillation column 10, and content of 2,2,4-trimethyl-1,3-pentanediol (TMPD) in the lower discharge stream of the first section D1 separating hydroxypivaldehyde were shown in the following Table 1.

Comparative Example 3

As in the process flow diagram illustrated in FIG. 4, simulations were performed using Aspen Plus manufactured by Aspen Corporation.

Specifically, crude hydroxypivaldehyde was fed as a feed stream to a first section D1 of a distillation column 10. At this time, the components of the feed stream are the same as in Example 1. In addition, the distillation column 10 was partitioned into a first section D1 and a second section D2 through a partition wall 11, a chimney tray 13 was provided above the first section D1, and the feed stream was fed to a position lower than the chimney tray 13.

Hydroxypivaldehyde was separated into the lower portion in the first section D1 of the distillation column 10, and the gaseous component moved directly to the second section D2.

Some of the upper discharge stream of the second section D2 was refluxed by using a condenser, and unreacted iso-butylaldehyde was separated into the remaining stream.

Some of the lower discharge stream of the second section D2 was refluxed using a reboiler and by-products were separated into the remaining stream, and some of the remaining stream was branched and refluxed to the first section D1.

Results of measuring a recovery rate of hydroxypivaldehyde (HPA) recovered from the lower portion of the first section D1 of the distillation column 10, a recovery rate of iso-butylaldehyde (i-BAL) recovered to the upper portion of the distillation column 10, energy consumption used in the distillation column 10, and content of 2,2,4-trimethyl-1,3-pentanediol (TMPD) in the lower discharge stream of the first section D1 separating hydroxypivaldehyde were shown in the following Table 1.

TABLE 1

|  | Example 1 | Comparative Example 1 | Comparative Example 2 | Comparative Example 3 |
|---|---|---|---|---|
| HPA recovery rate (%) | 99.994 | 99.994 | 99.994 | 99.994 |
| i-BAL recovery rate (%) | 91.123 | 91.123 | 91.123 | 91.123 |
| Energy consumption (%) | 81.1 | 100 | 81.1 | 81.1 |
| TMPD content (wt %) | 0.001 | 0.001 | 0.1 | 0.1 |

In the above Table 1, the energy consumption was indicated by converting the energy consumption measured in Example 1 and Comparative Examples 1 to 3, respectively, into a percentage with respect to the energy consumption used in Comparative Example 1.

In addition, the HPA recovery rate represents the ratio of the recovered content of hydroxypivaldehyde to the content of hydroxypivaldehyde included in the feed stream, and the i-BAL recovery rate represents the recovered content of iso-butylaldehyde to the content of iso-butylaldehyde contained in the feed stream.

In the above Table 1, in the case of Example 1, the multi-component mixture separation system using one distillation column 10 and a phase separator 20 equipped with a partition wall 11 according to the present disclosure was used, and it could be confirmed that the energy consumption was reduced compared to Example 1, and the recovery rate of the recovered hydroxypivaldehyde and the recovery rate of iso-butylaldehyde were the same as those of Comparative Example 1.

In comparison, in the case of Comparative Example 1, two distillation columns were used, and it could be confirmed that the upper discharge stream of the first distillation column 100 was condensed and then supplied to the phase separator 120 for phase separation, and the energy consumption increased compared to the Example by supplying an aqueous phase and an oil phase that were not refluxed to the first distillation column 100 among the phase-separated aqueous phase to the second distillation column 200 and heating the aqueous and oil phases again.

In addition, as in the above embodiment, in the case of Comparative Example 2 in which one distillation column 10 partitioned by a partition wall was used, but the chimney tray 13 was not provided above the first section D1, and there was no stream refluxed to the first section D1 due to the absence of the phase separator 20, the liquefied component containing a reactive organic material was introduced into the first section D1 from the second section D2 through an upper space of the distillation column 10, and the generation amount of TMPD, which was difficult to separate from hydroxypivaldehyde in the rear-stage process, increased. Specifically, in the case of Comparative Example 2, the content of TMPD in the lower discharge stream of the first section D1 separating hydroxypivaldehyde increases, so there is a problem in that it is difficult to control the quality of the product in the subsequent process.

In addition, as in the above embodiment, even in the case of Comparative Example 3 in which one distillation column 10 partitioned by a partition wall and the chimney tray 13 were provided in the first section D1 of the distillation column, but the phase separator 20 was not provided, the liquefied component from which the reactive organic material was not removed was introduced into the first section D1 due to the absence of the phase separator 20 to increase the content of the TMPD in the lower discharge stream of the first section D1 separating hydroxypivaldehyde, so there is a problem in that it is difficult to control the quality of the product in the subsequent process.

The invention claimed is:

1. A multi-component mixture separation system, comprising:
    a distillation column including a first section and a second section separated by a partition wall; and
    a phase separator receiving a lower discharge stream of the second section and separating the lower discharge stream into an aqueous phase and an oil phase, and refluxing a portion of the separated aqueous phase or oil phase to the first section,
    wherein the lower discharge stream is discharged from a bottom of the distillation column,
    wherein the first section includes a chimney tray provided on an upper portion of the first section, and
    wherein the first section is supplied with a feed stream containing three or more components, and the first section is configured to separate the feed stream into a gaseous component and a high boiling point component such that the high boiling point component descends to a lower portion of the first section and the gaseous component moves to the second section.

2. The multi-component mixture separation system of claim 1, wherein the partition wall extends upwardly from a lower end of the distillation column.

3. The multi-component mixture separation system of claim 1, wherein a stream refluxed from the phase separator to the first section is fed to a position higher than a height to which the feed stream is fed.

4. The multi-component mixture separation system of claim 1, wherein the chimney tray is formed to correspond to an upper area of the first section partitioned by the partition wall.

5. The multi-component mixture separation system of claim 1, further comprising:
    a liquid distribution device provided under the chimney tray.

6. The multi-component mixture separation system of claim 5, wherein a stream refluxed from the phase separator to the first section is refluxed to a position between the chimney tray and the liquid distribution device.

7. The multi-component mixture separation system of claim 5, wherein the feed stream is fed to a position lower than the liquid distribution device.

8. The multi-component mixture separation system of claim 1, wherein the second section of the distillation column separates a low-boiling point component to an upper portion, feeds the lower discharge stream to the phase separator, and then separates a medium-boiling point component from any one or more of the aqueous phase and the oil phase separated in the phase separator.

9. The multi-component mixture separation system of claim 1, wherein the phase separator refluxes a portion of the separated aqueous phase to the first section of the distillation column.

10. The multi-component mixture separation system of claim 1, wherein the feed stream is crude hydroxypivaldehyde containing hydroxypivaldehyde and iso-butylaldehyde.

11. The multi-component mixture separation system of claim 10, wherein the first section of the distillation column separates hydroxypivaldehyde to a lower portion, and the second section separates iso-butylaldehyde to an upper portion.

* * * * *